United States Patent

Krief et al.

[11] 4,048,215
[45] Sept. 13, 1977

[54] PROCESS FOR PREPARATION OF TRANS-CHRYSANTHEMATES

[75] Inventors: Alain Krief, Boninne; László Hevesi, Jambes, both of Belgium

[73] Assignee: Roussel Ulcaf, Paris, France

[21] Appl. No.: 673,458

[22] Filed: Apr. 5, 1976

[30] Foreign Application Priority Data
Apr. 7, 1975 Belgium .................. 155168

[51] Int. Cl.² ........................................ C07C 67/30
[52] U.S. Cl. .................................................. 560/124
[58] Field of Search .................................. 260/468 H

[56] References Cited

U.S. PATENT DOCUMENTS 3,723,469  3/1973  Martel .................. 260/468 H

FOREIGN PATENT DOCUMENTS 2,067,854  8/1971  France .................. 260/514 H

OTHER PUBLICATIONS

Grieco, Tetrahedron Letters, pp. 3781–3783 (1972).
Bestmann, Angew. Chem., 74, pp. 154–155 (1962).
Kirmse, "Carbene Chemistry" 2nd Ed., pp. 68, 69, 73 & 74 (Academic Press, 1971).
March, "Advanced Organic Chemistry: Reactions, Mechanisms, and Structure," pp. 702–709 (1968).

*Primary Examiner*—Bernard Helfin
*Assistant Examiner*—Michael Shippen
*Attorney, Agent, or Firm*—Hammond & Littell

[57] ABSTRACT

A novel process for the preparation of alkyl esters of dl-trans chrysanthemic acid of the formula

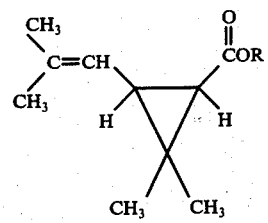

I wherein R is alkyl of 1 to 6 carbon atoms comprising reacting in the presence of a strong base an alkyl 4-oxo-2E-butenoate of the formula

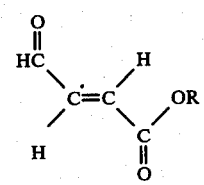

II with at least about 2 molar equivalents of a triphenyl isopropyl phosphonium halide which uses easily accessible starting materials.

6 Claims, No Drawings

PROCESS FOR PREPARATION OF TRANS-CHRYSANTHEMATES

STATE OF THE ART

Various procedures have been described in the patent literature for the production of alkyl esters of dl-trans chrysanthemic acid or 2,2-dimethyl-3RS-(2'-methyl-1'-propenyl)-cyclopropane-1RS-carboxylic acid such as U.S. Pat. Nos. 3,723,469, 3,445,499, 3,711,555 and 3,786,052 and U.S. Pat. No. Re. 27,592.

OBJECTS OF THE INVENTION

It is an object of the invention to provide an improved process for the preparation of lower alkyl esters of dl-trans chrysanthemic acid.

This and other objects and advantages of the invention will become obvious from the following detailed description.

THE INVENTION

The novel process of the invention for the preparation of lower alkyl esters of dl-trans chrysanthemic acid comprises reacting in the presence of a strong base a lower alkyl 4-oxo-2-E-butenoate of the formula:

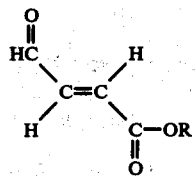

wherein R is alkyl of 1 to 6 carbon atoms with at least about 2 molar equivalents of a triphenyl isporopyl phosphonium halide.

It can be seen that it is more advantageous to use an excess rather than a deficit of the reactant and under these conditions, it is preferred use at least 2 equivalents of the triphenyl isopropyl phosponium halide since one equivalent reacts with the aldehyde group and the other equivalent reacts with the ethylenic double bond of the alkyl 4-oxo-2-E-butenoate. Experience has shown that more than 2 molar equivalents, such as 3 molar equivalents, have given satisfactory results.

Examples of suitable strong bases for the process are alkali metal hydrides such as sodium hydride, alkali metal amides such as sodium amide, alkali metal alcoholates such as potassium methanolate or alkyllithiums such as n-butyllithium. The triphenyl isopropyl phosphonium halide may be the chloride, bromide or iodide for example.

The said condensation reaction is preferably effected in an organic solvent such as tetahydrofuran, dimethyl sulfoxide, dimethoxy ethane, monoethyl ether of diethylene glycol, diethyl ether of diethylene glycol or ethyl ether.

The lower alkyl esters of formula I may be methyl, ethyl or branched or straight chain propyl, butyl, pentyl or hexyl. The starting materials for the process of the invention are easily obtainable compounds.

The lower alkyl esters of formula I are useful for the preparation of the corresponding dl-trans chrysanthemic acid by simple saponification. The dl-trans chrysanthemic acid has a great industrial interest since the esters thereof with certain alcohols produce very effective and very useful insecticides.

Examples of condensation of triaryl alkylidene phosphoranes with unsaturated esters are known in the literature leading to the preparation of gem dimethyl cyclopropane derivatives. [Grieco et al., Tet. Letters, 1972, p. 3781 and Dauben et al., Tet. Letters, 1966, p. 3771]. However, once the gem dimethyl cyclopropane ring is formed, it is only with great difficulty taht one can introduce into the cyclopropane ring the 2-methylpropen-1-yl group characteristic of chrysanthemic acid.

The merit of the present invention resides in the fct that it permits in a single step the synthesis of the chrysanthemic structure due to the judicious selection of alkyl 4-oxo-2-E-butenoates as the starting material. The alkyl 4-oxo-2-E-butenoates possess the advantage of permitting the simultaneous formation of the dimethyl cyclopropane ring by action of triphenyl isopropyl phosphonium halide with the double bond of the butenoate in the presence of a strong base and formation of the isopropylidene chain of chrysanthemic acid by action of the said phosphonium halide with the aldehyde group.

The reaction serving as the basis of the process of the invention presents equally from the point of view of the mechanism an unexpected character. As one can ascertain, in effect, when it is made to react first with alkyl 4-oxo-2-E-butenoate, a single molecule of triphenyl isopropyl phosphonium halide in the presence of a base, this first molecule reacts with the aldehyde group. After isolation of the diene formed, the reaction with a second molecule of the phosphonium salt does not lead to obtention of the chrysanthemic structure. Although this phenomenon is not totally understood yet, it shows well the surprising character of the reaction which is the basis of the process of the invention.

The methyl, ethyl and propyl esters of 4-oxo-2-E-butenoic acid are as described by Rambaud et al. [Bull. Soc. Chim. (1961), p. 1567]. They are obtained by oxidation of the corresponding alkyl esters of 1-hydroxy-2-butenoic acid with chromic acid anhydride. The other alkyl esters may be made in a similar fashion.

In the following examples there are described several preferred embodiments to illustrate the invention. However, it should be understood that the invention is not intended to be limited to the specific embodiments.

EXAMPLE 1 methyl 2,2-dimethyl-3RS-(2'-methyl-1'-propenyl)-cyclopropane-1RS-carboxylate 2 ml of a 1.75N solution of n-butyllithium in hexane were added at 0° C to a solution of 1.9 g of triphenyl isopropyl phosphonium iodide in 30 ml of tetrahydrofuran and the mixture was stirred at 25° C for 30 minutes and was then cooled to −78° C. A solution of 0.230 g of methyl 4-oxo-2E-butenoate in 1 ml of tetrahydrofuran was added to the reaction mixture which was then stirred at −78° C for 5 minutes. The temperature was allowed to return to 20° C and was then stirred for 15 hours. Water was added to the reaction mixture which was then extracted with ethyl ether and the ether extracts were dried and concentrated to dryness. The residue was chromatographed over silica gel and elution with a 1—1 ethyl etherpentane mixture yielded 0.190 g of raw methyl 2,2-dimethyl-3RS-(2'-methyl-1'-propenyl)-cyclopropane-1RS-carboxylate.

A mixture of the said raw ester, 7.5 ml of methanol and 7.5 ml of a methanolic soluton of 20% potassium hydroxide was stirred for 15 hours at 20° C and the methanol was distilled under reduced pressure. The residue was added to water and the mixture was extracted with ether. The aqueous phase was acidified with concentrated hydrochloric acid and was extracted with ether. The ether extract was dried and evaporated to dryness to obtain 0.030 g of 2,2-dimethyl-3RS-(2'-methyl-1'-propenyl)-cyclopropane-1RS-carboxylic acid.

EXAMPLE 2 methyl 2,2-dimethyl-3RS-(2'-methyl-1'-propenyl)-cyclopropane-1RS-carboxylate 14.1 ml of a 1.75N solution of N-butyllithium in hexane were added to a mixture of 14.26 g of triphenyl isopropyl phosphonium iodide in 100 ml of tetahydrofuran and after cooling the mixture to −78° C, 1.14 g of methyl 4-oxo-2-butenonate were added thereto. The mixture was stirred at −78° C for 5 minutes and after returning the temperature to 20° C the mixture was stirred for 60 hours. Water was added to the mixture which was then extracted with ether. The ether extracts were dried and evaporated to dryness by distillation. The residue was added to pentane and the mixture was filtered to remove insoluble triphenyl phosphine. The filtrate was evaporated to dryness under reduced pressure and the residue was rectified at 15 mm Hg to obtain 0.88 g of a product with a boiling point of 95°–110° C and 0.2 g of a product with a boiling point of 120°–180° C. The two combined fractions were methyl 2,2-dimethyl-3RS-(2'-methyl-1'-propenyl)-cyclopropane-1RS-carboxylate which was saponified with methanolic potassium hydroxide as in Example 1. The ether extract was acidified, dried and concentrated to dryness to obtain 0.8 g of a product. The product was crystallized 5 times from pentane to obtain 0.230 g of 2,2-dimethyl-3RS-(2'-methyl-1'-propenyl)-cyclopropane-1RS-carboxylic acid melting at 54° C.

Various modifications of the process of the invention may be made without departing from the spirit or scope thereof and it is to be understood that the invention is to be limited only as defined in the appended claims.

We claim:

1. A process for the preparation of an ester of the formula

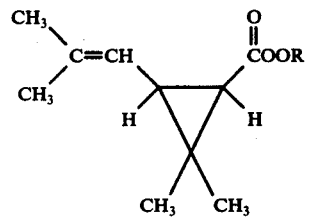

wherein R is alkyl of 1 to 6 carbon atoms comprising reacting at least 2 molar equivalent of a triphenyl isopropyl phosphonium halide based on the 4-oxo-2E-butenoate with a strong base and reacting the resulting ylide with an alkyl 4-oxo-2E-butenoate of the formula

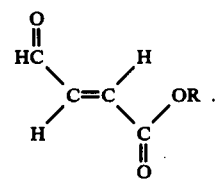

2. The process of claim 1 wherein 2 to 3 molar equivalents of the phosphonium halide are used.

3. The process of claim 1 wherein the strong base is n-butyllithium.

4. The process of claim 1 wherein R is methyl.

5. The process of claim 1 wherein the phosphonium halide is the iodide.

6. A process for preparation of methyl 2,2-dimethyl-3RS-(2'-methyl-1'-propenyl)-cyclopropane-1RS-carboxylate comprising reacting methyl 4-oxo-2-butenoate with 3 molar equivalents of triphenyl isopropyl phosphonium iodide in an organic solvent in the presence of n-butyllithium.

* * * * *